United States Patent [19]

Nolte

[11] Patent Number: 4,982,052
[45] Date of Patent: Jan. 1, 1991

[54] SEPARATION OF A MIXTURE OF NORMAL PARAFFINS BRANCHED CHAIN PARAFFINS AND CYCLIC PARAFFINS

[75] Inventor: David G. Nolte, Houston, Tex.

[73] Assignee: Texaco Inc., White Plains, N.Y.

[21] Appl. No.: 288,839

[22] Filed: Dec. 23, 1988

[51] Int. Cl.$^5$ .............................................. C07C 7/12
[52] U.S. Cl. ............................... 585/822; 208/310 Z; 585/826
[58] Field of Search ............... 585/820, 822, 827, 831, 585/836, 837; 208/310 Z

[56] References Cited

U.S. PATENT DOCUMENTS

| | | | |
|---|---|---|---|
| 3,054,838 | 9/1962 | Egan | 585/822 |
| 3,303,231 | 2/1967 | Hicks et al. | 585/822 X |
| 4,350,501 | 9/1982 | Bannon | 585/826 X |
| 4,367,364 | 1/1983 | Kulprathipanja et al. | 585/826 |
| 4,855,529 | 8/1989 | Stem et al. | 585/822 X |

FOREIGN PATENT DOCUMENTS

| | | | |
|---|---|---|---|
| 124725 | 9/1980 | Japan | 585/822 |
| 842139 | 7/1960 | United Kingdom | 585/822 |

*Primary Examiner*—Glenn Caldarola
*Attorney, Agent, or Firm*—Jack H. Park; Kenneth R. Priem; Harold J. Delhommer

[57] ABSTRACT

The invention is a process for separating a mixture of saturated hydrocarbons into normal paraffins, branched chain paraffins, and cyclic paraffins which comprises contacting said mixture with a series of two molecular sieves comprising a first silicalite and a second silicalite which have different retention conditions. One of the silicalites is selected so that it will retain normal paraffins and pass through branched chain paraffins and cyclic paraffins. The second silicalite is selected so that it will retain normal and branched chain paraffins and pass through cyclic paraffins. The two molecular sieves are employed in series so that the mixture of saturated hydrocarbons can be separated into normal paraffins, branched chain paraffins, and cyclic paraffins.

13 Claims, No Drawings ized routine paraffin distribution data for bitumen and oil analysis.

The disclosed invention separates a mixture of saturated hydrocarbons into three fractions in a fraction of the time done by previous methods involving open column separation. The invention separation can be performed and the molecular sieve regenerated in as little as 90 minutes. The silicalite columns can be run with repeated flow reversals at high temperatures and pressures with no significant degradation. The procedure can also be completely automated.

The invention process comprises contacting a mixture of saturated hydrocarbons with a series of at least two molecular sieves comprising a first and a second silicalite having different retention characteristics. One silicalite will pass through cyclic paraffins and retain normal paraffins and branched chain paraffins. A second silicalite will retain only normal paraffins and pass through branched chain paraffins and cyclic paraffins. By appropriate backflushing of the molecular sieves and placement of the two molecular sieves in series, a saturated hydrocarbon mixture can be easily divided into its three main fractions.

The preferred invention embodiment comprises a multistep method, the first step of which is contacting said mixture of saturated hydrocarbons at retention conditions with a molecular sieve comprising a first silicalite having a pore size and crystal structure which will retain normal paraffins and pass through branched chain paraffins and cyclic paraffins. Before silicalite contact, the mixture is preferably injected with a mobile phase of a branched chain alkane having from about 5 to about 8 carbon atoms, most preferably, iso-octane. This injection is generally carried out by placing said mixture in a sample loop and injecting the contents of the sample loop as a slug following and preceding the mobile phase. It is believed that in most cases the mixture of saturated hydrocarbons must be dissolved in a solvent to get all of the mixture into the sample loop. The dissolving solvent is preferably the solvent used for the mobile phase.

The unretained mixture of branched chain paraffins and cyclic paraffins is then contacted at retention conditions with a molecular sieve comprising a second silicalite having a pore size and crystal structure which will retain branched chain paraffins and pass through cyclic paraffins. The second silicalite is heated to a temperature of at least 70° C., preferably at least 90° C. The normal paraffins are recovered by displacing the normal paraffins from the first silicalite with a displacement material. The branched chain paraffins are recovered by displacing the branched chain paraffins from the second silicalite with a displacement material. The cyclic paraffins unretained from the second silicalite are also recovered.

The first silicalite preferably has a pore size of about 5.4±0.2 angstroms. The second silicalite preferably has a pore size greater than or equal to about 6.2 angstroms.

The normal paraffins retained by the first silicalite molecular sieve can be displaced by backflushing the first silicalite with a displacement material of a normal alkane, or a mixture of a normal alkane and a branched chain alkane, each having from about 5 to about 8 carbon atoms. The branched chain paraffins, or the branched chain paraffins and the normal paraffins which may be retained in the second silicalite, can also be displaced by backflushing the second silicalite with a displacement material of a normal alkane or a mixture of

SEPARATION OF A MIXTURE OF NORMAL PARAFFINS BRANCHED CHAIN PARAFFINS AND CYCLIC PARAFFINS

BACKGROUND OF THE INVENTION

This invention relates to hydrocarbon separation. More particularly, the invention concerns a process for separating a mixture of saturated hydrocarbons into normal paraffins, branched chain paraffins, and cyclic paraffins with the use of multiple molecular sieves of silicalite.

There are an abundance of processes known to separate classes of hydrocarbons using solid adsorbents. The most common adsorbents used for hydrocarbon separation are the crystalline aluminosilicates, the best known of which are the zeolites. The crystalline aluminosilicates function as molecular sieves. They contain pores having cross-sectional diameters which will accept certain molecules of a mixture of molecules while rejecting other molecules having different sizes, thereby separating the accepted molecules from the mixture.

A new molecular sieve adsorbent material known as silicalite has been disclosed and claimed in U.S. Pat. No. 4,061,724. The disclosed separation process discusses in general terms the separation of an organic compound from an aqueous solution. The separations exemplified in the above reference are n-butanol, methylcellosolve, methanol and phenol.

U.S. Pat. No. 4,455,445 discloses a separation of n-butane from isobutylene by the use of a silicalite molecular sieve. U.S. Pat. No. 4,486,618 discloses the separation of n-hexane from other paraffins having 6 carbon atoms using a silicalite molecular sieve. U.S. Pat. No. 4,455,444 discloses the separation of normal paraffins from a mixture of branched chain and cyclic paraffins by the use of a silicalite molecular sieve at 120° C. to 140° C. However, none of the above references disclose the separation of branched chain paraffins from cyclic paraffins.

SUMMARY OF THE INVENTION

The invention is a process for separating a mixture of saturated hydrocarbons into normal paraffins, branched chain paraffins, and cyclic paraffins which comprises contacting said mixture with a series of two molecular sieves comprising a first silicalite and a second silicalite which have different retention conditions. One of the silicalites is selected so that it will retain normal paraffins and pass through branched chain paraffins and cyclic paraffins. The second silicalite is selected so that it will retain normal and branched chain paraffins and pass through cyclic paraffins. The two molecular sieves are employed in series so that the mixture of saturated hydrocarbons can be separated into normal paraffins, branched chain paraffins, and cyclic paraffins.

DETAILED DESCRIPTION

The separation of saturated hydrocarbons into normal paraffins, branched chain paraffins and cyclic paraffins is difficult to do with a relatively high degree of purity so that components of interest are unobscured. But for petroleum geochemistry analysis, this separation is important, and relatively pure fractions are desirable. The geochemistry uses are for oil-to-oil correlations and oil-to-source correlations, as well as improva normal alkane and a branched chain alkane having from about 5 to about 8 carbon atoms.

It has been discovered that the use of heavier paraffins as the mobile displacement phase during backflushing shorten the elution time. Normal octane provides the practical limit of heavier molecular weight beyond which components of interest are lost during solvent removal to recover the retained or eluted fraction. Since the cost of normal octane is about 8 times that of iso-octane, additional tests were performed to see if a mixture of n-octane and iso-octane would work effectively. It was discovered that a 50/50 mixture and a 33/67 vol/vol mixture of n-octane and iso-octane were just as effective as using 100% n-octane. No attempt, however, was made to optimize the mixture. 100% iso-octane was not effective.

It has also been discovered that increasing the temperature of the column generally shortens the elution time. The maximum temperature employed was limited to 99° C. by the Spectra Physics High Performance Liquid Chromatograph (HPLC) employed. It is also believed that with proper mobile phase gradient and temperature programming to increase and decrease temperature during backflushing, the normal paraffin fraction retained by the first silicalite molecular sieve may be programmed to elute so as to simulate a distillation.

After recovery of the three fractions from the first and second silicalite sieves, the equipment must be regenerated for reuse. One method of regenerating the first and second silicalites is by backflushing both silicalites with an inert gas. Preferably, this inert gas is helium, argon, or nitrogen. Most preferably, the columns are backflushed with helium at a pressure of at least 50 psi for at least 20 minutes, preferably 100 psi for about 20 to 40 minutes.

After regeneration with helium, the columns should be restabilized by backflushing with a branched chain alkane having from about 5 to about 8 carbon atoms, preferably iso-octane.

This invention method has been tested with an HPLC system and compared with open column separation methods. Not only was the invention method able to perform the separations with regenerated columns in about 90 minutes compared with the 1 to 2 days and substantially more technician labor of the prior art, but the recovered fractions of saturated hydrocarbons were much purer than the open column separation of the prior art. Instrumentation employed consisted of a Spectra Physics Model SP8000B HPLC. The standard 6 pore injection valve was replaced with a 10 pore Valco valve to facilitate backflushing. A second valve with an electric actuator, a Valco Model EC4W, was added to permit replacement of the liquid mobile phase with helium gas during column regeneration. All fractions were qualitatively analyzed by gas chromatography. Analysis indicated that cross contamination in the recovered fractions was less than with previous methods used.

The silicalites employed were selected so that the first silicalite which retains normal paraffins and passes through branched chain paraffins and cyclic paraffins was a silicalite sold under the trademark Type S-115 by Union Carbide. It has a novel topological type of tetrahedral framework which encloses a three dimensional system of intersecting channels defined by 10 rings wide enough to adsorb molecules with kinetic diameters approaching 6 angstroms and room temperature. The pore size of the first silicalite is about 5.4±0.2 angstroms. The S-115 silicalite has a composition of greater than 99% $SiO_2$. The free aperture size for the zig-zag channels is 5.4 angstroms, while the straight channels have a cross-section of approximately 5.75 by 5.15 angstroms. Pore volume is about 0.19 cc/g with a crystal density of about 1.76 g/cc. The sample used contained ⅛" S-115 extrudates bonded with 15% $SiO_2$.

The second silicalite was selected so that it would retain normal paraffins and branched chain paraffins and pass through cyclic paraffins. The silicalite employed was sold under the trademark Type S-130 by Union Carbide. It has a pore size opening equal to or greater than 6.2 angstroms. The S-130 silicalite is a hydrophobic and organophilic material with a tetrahedral framework structure. Its anhydrous composition is greater than 99% $SiO_2$. It has a pore volume of about 0.15 cc/g and a mean particle size (Coulter counter) of 3.7 micrometers and a surface area (1 pt. BET, $N_2$) of 379 $m^2/g$.

Both silicalites were hand packed in columns of 6.2 mm inner diameter by 250 mm in length with 170 to 250 mesh bonded silicalite sized from crushed pellets. The empty column volume was 7.6 cc and the silicalite volume was 3.4 cc, leaving an interstitial volume of 4.2 cc. The total pore volume of the silicalite was 1.1 cc.

Many other variations and modifications may be made in the concepts described above by those skilled in the art without departing from the concepts of the present invention. Accordingly, it should be clearly understood that the concepts disclosed in the description are illustrative only and are not intended as limitations on the scope of the invention.

What is claimed is:

1. A process for separating a mixture of saturated hydrocarbons into normal paraffins, branched chain paraffins, and cyclic paraffins, which comprises:
    contacting said mixture at retention conditions with a molecular sieve comprising a first silicalite having a pore size and crystal structure which will retain normal paraffins, and pass through branched chain paraffins and cyclic paraffins;
    contacting at retention conditions the unretained mixture of branched chain paraffins and cyclic paraffins with a molecular sieve comprising a second silicalite having a pore size and crystal structure which will retain branched chain paraffins and pass through cyclic paraffins,
    said second silicalite heated to a temperature of at least 70° C.;
    recovering the cyclic paraffins unretained by the second silicalite;
    recovering the normal paraffins by displacing the normal paraffins from the first silicalite with a displacement material; and
    recovering the branched chain paraffins by displacing the branched chain paraffins from the second silicalite with a displacement material.

2. The method of claim 1, wherein the first silicalite has a pore size of about 5.4±0.2 angstroms.

3. The method of claim 1, wherein the second silicalite has a pore size greater than or equal to about 6.2 angstroms.

4. The method of claim 1, wherein the first and second silicalite are packed into separation columns.

5. The method of claim 1, wherein said mixture is injected with a mobile phase of a branched chain alkane having from about 5 to about 8 carbon atoms.

6. The method of claim 1, wherein the branched chain paraffins are displaced by backflushing the second silicalite with a displacement material of a normal alkane, or a mixture of a normal alkane and a branched chain alkane, each having from about 5 to about 8 carbon atoms.

7. The method of claim 1, wherein the normal paraffins are displaced by backflushing the first silicalite with a displacement material of a normal alkane or a mixture of a normal alkane and a branched chain alkane having from about 5 to about 8 carbon atoms.

8. The method of claim 1, further comprising regenerating the first silicalite and the second silicalite by backflushing both silicalites with an inert gas.

9. The method of claim 8, wherein the inert gas is helium, argon, or nitrogen.

10. The method of claim 8, further comprising backflushing with helium at least 50 psi for at least 20 minutes.

11. The method of claim 8, further comprising re-stabilizing the column by backflushing with a branched chain alkane having from about 5 to about 8 carbon atoms after regenerating with an inert gas.

12. A process for separating a mixture of saturated hydrocarbons into normal paraffins, branched chain paraffins, and cyclic paraffins, which comprises:
dissolving said mixture in a solvent of iso-octane;
injecting said mixture in a solvent with a mobile phase of iso-octane;
contacting said mixture at retention conditions with a molecular sieve comprising a first silicalite having a pore size of about 5.4±0.2 angstroms which will retain normal paraffins, and pass through branched chain paraffins and cyclic paraffins;
contacting at retention conditions the unretained mixture of branched chain paraffins and cyclic paraffins with a molecular sieve comprising a second silicalite having a pore size greater than or equal to about 6.2 angstroms which will retain branched chain paraffins and pass through cyclic paraffins,
said second silicalite heated to a temperature of at least 90° C.;
recovering the cyclic paraffins unretained by the second silicalite;
recovering the normal paraffins by backflushing the normal paraffins from the first silicalite with octane; and
recovering the branched chain paraffins by backflushing the branched chain paraffins from the second silicalite with octane.

13. A process for separating a mixture of saturated hydrocarbons into normal paraffins, branched chain paraffins, and cyclic paraffins, which comprises:
contacting said mixture at retention conditions with a molecular sieve comprising a second silicalite having a pore size and crystal structure which will retain normal paraffins and branched chain paraffins and pass through cyclic paraffins,
said second silicalite heated to a temperature of at least 70° C.;
recovering the normal paraffins and branched chain paraffins by displacing the normal paraffins and branched chain paraffins from the second silicalite with a displacement material;
contacting at retention conditions the mixture of normal paraffins and branched chain paraffins displaced from the second silicalite with a molecular sieve comprising a first silicalite having a pore size and crystal structure which will retain normal paraffins and pass through branched chain paraffins;
recovering the cyclic paraffins unretained by the second silicalite;
recovering the branched chain paraffins unretained by the first silicalite; and
recovering the normal paraffins retained by the first silicalite by displacing the normal paraffins from the first silicalite with a displacement material.

* * * * *